(12) United States Patent
Rajasekharan et al.

(10) Patent No.: US 9,476,866 B2
(45) Date of Patent: Oct. 25, 2016

(54) COD/TOC ANALYSES USING FERRATE OXIDATION

(71) Applicant: Hach Company, Loveland, CO (US)

(72) Inventors: Vishnu V. Rajasekharan, Fort Collins, CO (US); John Lee, Fort Collins, CO (US); Richard E. Leggett, Dickinson, TX (US)

(73) Assignee: Hach Company, Loveland, CO (US)

( * ) Notice: Subject to any disclaimer, the term of this patent is extended or adjusted under 35 U.S.C. 154(b) by 17 days.

(21) Appl. No.: 14/521,683

(22) Filed: Oct. 23, 2014

(65) Prior Publication Data

US 2015/0110677 A1 Apr. 23, 2015

Related U.S. Application Data

(60) Provisional application No. 61/894,906, filed on Oct. 23, 2013, provisional application No. 61/981,659, filed on Apr. 18, 2014.

(51) Int. Cl.
*G01N 33/18* (2006.01)
*B01L 3/00* (2006.01)
*G01N 21/80* (2006.01)
*G01N 31/22* (2006.01)

(52) U.S. Cl.
CPC ........... *G01N 33/1806* (2013.01); *B01L 3/502* (2013.01); *B01L 3/5635* (2013.01); *G01N 21/80* (2013.01); *G01N 33/1846* (2013.01); *B01L 3/5082* (2013.01); *B01L 2200/16* (2013.01); *G01N 31/221* (2013.01)

(58) Field of Classification Search
CPC .... B01L 3/502; B01L 3/5635; B01L 3/5082; B01L 33/1806; B01L 2200/16; G01N 33/1806; G01N 33/1846; G01N 21/78; G01N 21/80; G01N 31/221

See application file for complete search history.

(56) References Cited

U.S. PATENT DOCUMENTS

| | | | |
|---|---|---|---|
| 2,758,090 A | 8/1956 | Mills et al. | |
| 4,783,394 A | 11/1988 | Hirose et al. | |
| 6,183,695 B1 | 2/2001 | Godec et al. | |
| 6,623,974 B1 | 9/2003 | Horan et al. | |
| 8,449,756 B2 | 5/2013 | Monzyk et al. | |
| 2001/0051378 A1 | 12/2001 | Radmacher | |
| 2004/0136874 A1* | 7/2004 | Klimant | G01N 33/1846 422/501 |
| 2005/0282286 A1* | 12/2005 | Rieger | G01N 33/1846 436/146 |
| 2007/0189923 A1 | 8/2007 | Lenhard et al. | |

FOREIGN PATENT DOCUMENTS

| | | |
|---|---|---|
| CN | 102912366 A | 2/2013 |
| DE | 68903367 T2 | 5/1993 |
| DE | 60131747 T2 | 11/2008 |

(Continued)

OTHER PUBLICATIONS

International Search Report corresponding to Application No. PCT/US2014/061958, mailed on Mar. 25, 2015.

(Continued)

*Primary Examiner* — Jill Warden
*Assistant Examiner* — Julie Tavares
(74) *Attorney, Agent, or Firm* — Merchant & Gould P.C.

(57) ABSTRACT

Apparatuses for analyzing total carbon and chemical oxygen demand in a sample are disclosed. Also disclosed is a method for analyzing carbon and chemical oxygen demand.

12 Claims, 11 Drawing Sheets

(56) References Cited

FOREIGN PATENT DOCUMENTS

| | | |
|---|---|---|
| EP | 0082590 B1 | 9/1985 |
| EP | 0471784 B1 | 7/1996 |
| WO | 02/06160 A2 | 1/2002 |

OTHER PUBLICATIONS

Karlis Svanks, "Oxidation of Ammonia in Water by Ferrates (VI) and (IV)," Water Resources Center, Engineering Experiment Station, The Ohio State University, 1976.
Wayne Boyles, "The Science of Chemical Oxygen Demand," Technical Information Series, Booklet No. 9, 1997, pp. 1-24.
Rohan Gandhi, "Treatment of Combined Sewer Overflows Using Ferrate (VI)," The School of Graduate and Postdoctoral Studies, The University of Western Ontario, 2013.
J.-Q. Jiang et al., "Progress in the development and use of ferrate(VI) salt as an oxidant and coagulant for water and wastewater treatment", Water Research, 2002, vol. 36, pp. 1397-1408.
Claude A. O. Rosell "The Ferrates," J. Am. Chem. Soc, 1895, vol. 17, No. 10, pp. 760-769.
Ferrate—Layman's Explanation, available at http://www.ferrate.eu/pdf/laymanexplanation.pdf, accessed Jul. 7, 2015.
D. Tiwari et al., "Ferrate(VI) in the Treatment of Wastewaters: A New Generation Green Chemical," Waste Water—Treatment and Reutilization, 2011, pp. 241-276.
http://www.youtube.com/watch?v=2L906yG0-14, Versuche mit Ferrat(VI) (Experiments with ferrate(VI)), published on Jun. 6, 2013, accessed: Dec. 23, 2014.
James D. Carr, "Use of Potassium Ferrate in Oxygen Demand Measurement," Report No. EPA-600/7-77-099, 1977.
R. K. Sharma, "Textbook of Coordination Chemistry", Discovery Publishing House, 2007, pp. 124-125.
Gary Wulfsberg, "Principles of Descriptive Inorganic Chemistry", University Science Books, 1991, pp. 142-143.
A. F. Holleman et al., "Inorganic Chemistry", Academic Press, 1995, pp. 1457-1458.
Gary M. Brittenham, "The Development of Iron Chelators for Clinical Use", CRC Press, 1994, pp. 37-38.
K. M. MacKay et al., "Introduction to Modern Inorganic Chemistry", 6th edition, 2002, pp. 334-335.
Amit Arora "Text Book of Inorganic Chemistry", Discovery Publishing House, 2005, pp. 691-692.
http://www.wou.edu/las/physci/ch412/pourbaix.htm, last modified: Nov. 6, 2012; accessed: Dec. 23, 2014.
http://en.wikipedia.org/wiki/Chromium, last modified: Dec. 13, 2014; accessed: Dec. 23, 2014.
Virender K. Sharma, "Potassium ferrate(VI): an environmentally friendly oxidant," Advances in Environmental Research, 2002, vol. 6, pp. 143-156.
G. Hill et al., "Chemistry in Context", 5th edition, 2000, p. 202.
S. B. Quek et al., "Bio-Electrochemical Sensor for Fast Analysis of Assimilable Organic Carbon in Seawater," Journal of Biosensors & Bioelectronics, 2014, vol. 5, No. 2, pp. 1-4.
L. Li et al., "Determination of chemical oxygen demand of nitrogenous organic compounds in wastewater using synergetic photoelectrocatalytic oxidation effect at TiO2 nanostructured electrode," Analytica Chimica Acta 754, 2012, pp. 47-53.
G. W. Thompson et al., "Preparation and Purification of Potassium Ferrate. VI," J. Am. Chem. Soc., 1951, vol. 73, No. 3, pp. 1379-1381.
D. Y. Stupin et al., "Features of Chemiluminescence Arising in Oxidation of Luminol with Ferrate(VI) Ions in Alkaline Solutions", Russian Journal of General Chemistry, 2001, vol. 71, No. 5, pp. 659-663.
I. Ciabatti et al. "Treatment and reuse of dyeing effluents by potassium ferrate", Desalination, 2010, vol. 250, pp. 222-228.
V. Shastry et al. "Waste Water Treatment Using Eco Friendly Oxidising Agent Fe (VI)", Hydrology Current Research, 2011, vol. 2, No. 5, pp. 1-4.
N. Graham et al. "The influence of pH on the degradation of phenol and chlorophenols by potassium ferrate", Chemosphere, 2004, vol. 56, pp. 949-956.
B. Yang et al. "Removal of selected endocrine disrupting chemicals (EDCs) and pharmaceuticals and personal care products (PPCPs) during ferrate(VI) treatment of secondary wastewater effluents", Water Research, 2012, vol. 46, pp. 2194-2204.
V. K. Sharma et al. "Ferrate(VI) Enhanced Photocatalytic Oxidation of Pollutants in Aqueous TiO2 Suspensions", Envioron. Sci. Pollut. Res., 2008, vol. 15, No. 1, pp. 1-11.
Y. Lee et al., "Ferrate (Fe(VI)) Application for Municipal Wastewater Treatment: A Novel Process for Simultaneous Micropollutant Oxidation and Phosphate Removal", Environ. Sci. Technol., 2009, vol. 43, pp. 3831-3838.
V. K. Sharma et al., "Ferrates (iron(VI) and iron(V)): Environmentally friendly oxidants and disinfectants", Journal of Water and Health, 2005, pp. 1-15.
P. J. Dorathi et al. "Sonochemical degradation of p-chlorophenol in aqueous solution using hypervalent iron", Indian Journal of Chemical Technology, 2010, vol. 17, pp. 111-119.
C. Li et al., "A study of the preparation and reactivity of potassium ferrate", Chemosphere, 2005, vol. 61, pp. 537-543.
E. S. Batarseh et al., "Liquid Sodium Ferrate and Fenton's Reagent for Treatment of Mature Landfill Leachate", Journal of Environmental Engineering, 2007, pp. 1042-1050.
H. J. Zhang et al. "Electrogeneration of ferrate (VI) in low concentration NaOH solution for flow-injection-chemiluminescence detection", Chinese Chemical Letters, 2010, vol. 21, pp. 951-954.
T. Berner et al., "Toxicological Review of Hexavalent Chromium," EPA, 2010.
Edward Todd Urbansky, "Total organic carbon analyzers as tools for measuring carbonaceous matter in natural waters", Journal of Environmental Monitoring, 2001, vol. 3, No. 1, pp. 102-112.
V. K. Sharma et al., "Oxidation of Ammonia by Ferrate(VI)", Journal of Environmental Science and Health, 1998, vol. A33, No. 4, pp. 635-650.
J.-Q. Jiang et al., "The online generation and application of ferrate(VI) for sewage treatment-A pilot scale trial", Separation and Purification Technology, 2009, vol. 68, No. 2, pp. 227-231.
International Search Report corresponding to Application No. PCT/US2014/061952, mailed on Jan. 20, 2015.
International Search Report corresponding to Application No. PCT/US2014/061971, mailed on Jan. 26, 2015.

* cited by examiner

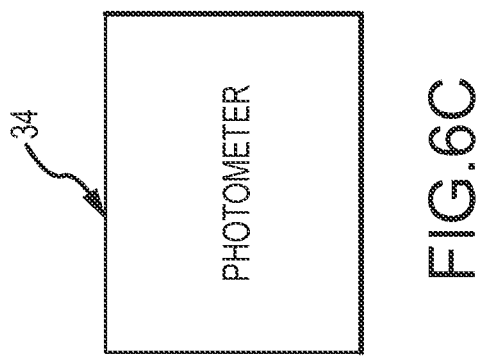
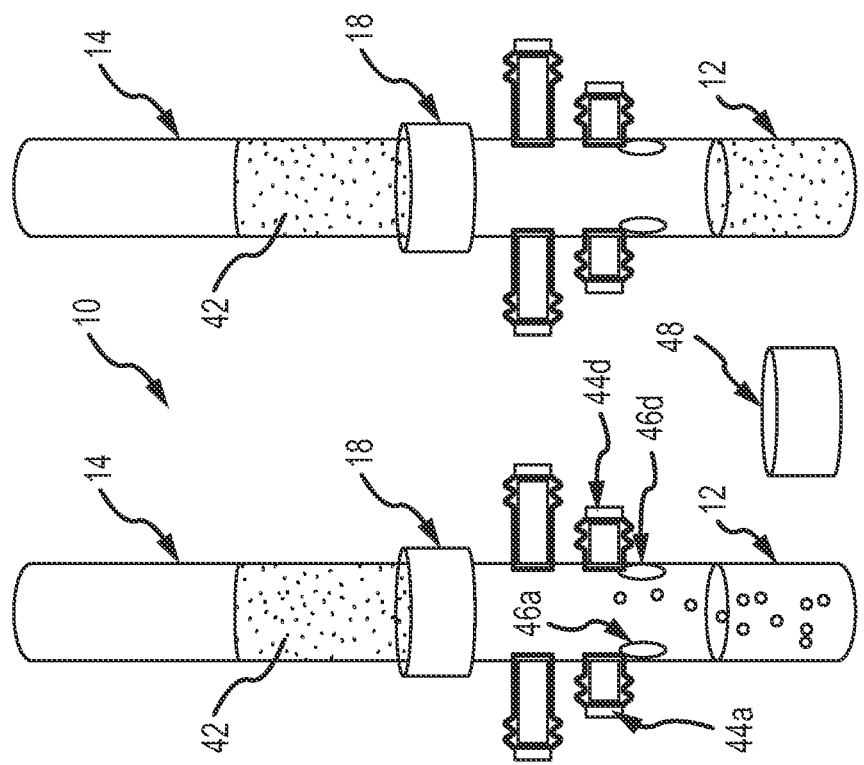

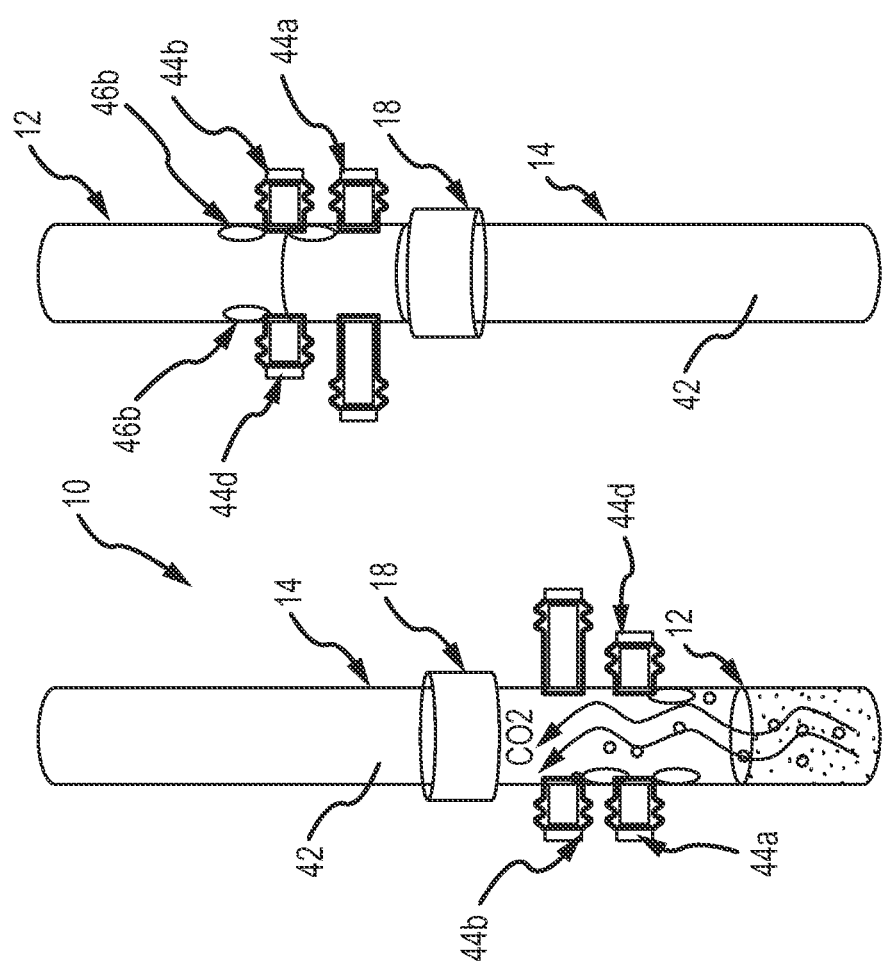

COD/TOC ANALYSES USING FERRATE OXIDATION

CROSS-REFERENCE TO RELATED APPLICATIONS

This application claims priority to U.S. provisional application No. 61/894,906 filed Oct. 23, 2013 and U.S. provisional application No. 61/981,659 filed Apr. 18, 2014.

INTRODUCTION

This application relates generally to carbon analysis and analysis of oxygen demand in aqueous samples and, more particularly, to the measurement of one or more of the Total Inorganic Carbon (TIC), Total Organic Carbon (TOC), Total Carbon (TC), and Chemical Oxygen Demand (COD) in the same aqueous sample using nontoxic high valence iron species as an oxidizer for the organic carbon and/or nitrogen components in the sample.

Oxygen demand is an important parameter for determining the amount of organic material in water. The test has its widest application in measuring waste loadings of treatment plants and in evaluating the efficiency of treatment processes. Other applications include testing lake and stream water samples for organic pollution. Oxygen demand testing does not determine the concentration of a specific substance; rather, it measures the effect of a combination of substances and conditions. Because oxygen demand is not a pollutant, it poses no direct threat to fish or other life. It can, however, pose an indirect threat to living organisms by reducing the level of dissolved oxygen. There are three widely-used methods of measuring oxygen demand. Two measure oxygen demand directly: Biochemical Oxygen Demand (BOD) and Chemical Oxygen Demand (COD). A third method- Total Organic Carbon (TOC)-measures oxygen demand indirectly using correlation, wherein a repeatable empirical relationship is established between TOC and COD for a specific water source. Such a relationship is established independently for each water source.

The organic carbon in water and wastewater includes a variety of organic compounds in various oxidation states. Some of these compounds can be further oxidized by chemical means, and chemical oxygen demand methods may be used to quantify these fractions. TOC provides a more direct measure of the total organic content of a sample than COD, but does not provide the same information. Unlike COD, TOC is independent of oxidation state of the organic matter and does not measure other organically bound elements, such as nitrogen and hydrogen, and inorganics that contribute to the oxygen demand measured by COD; therefore, TOC measurements do not replace COD determinations.

COD tests use a strong chemical oxidant in an acid solution and heat to oxidize organic material to $CO_2$ and $H_2O$ and other oxidation products. By definition, chemical oxygen demand is a measure of the oxygen equivalent of the organic matter content of a sample that is susceptible to oxidation by that specific strong chemical oxidant. Oxygen demand is determined by measuring the amount of oxidant consumed using titrimetric or photometric methods. The test is not adversely affected by toxic substances, and test data is available in 1½ to 3 hours, providing fast water quality assessment and process control.

Chemical species presently used to assess COD include potassium dichromate ($K_2Cr_2O_7$). Many types of waste are digested completely in less than 120 min. at 150° C. After the oxidation step is completed, the amount of dichromate consumed is determined titrimetrically or colorimetrically. Either the amount of reduced chromium (trivalent) or the amount of unreacted dichromate (hexavalent) can be measured. End products of the reaction are carbon dioxide, water, partially oxidized material, and various states of the chromium ion. Colorimetric procedures are easier and quicker to run and are generally more accurate. However, when samples are turbid or colored, or if a spectrophotometer is not available, a titrimetric procedure is used. The lowest range and highest sensitivity colorimetric COD test available has a detection range from 0.7 to 40 mg/L COD, where measurements are made at a wavelength of 350 nm, and between 3 and 150 mg/L at 420 nm. Complete digestion can be recognized by taking many consecutive colorimetric readings on a single sample, to determine when the changes are statistically insignificant. In typical wastewater samples, the presence of chloride does not affect the biological oxygen demand. However, the measurement of chemical (dichromate) oxygen demand is affected by chloride because chloride is oxidized by dichromate.

Hexavalent chromium ("Cr(VI)" or "chromium-6") is a known carcinogen and mutagen and so exposure and disposal are of great concern. In its draft "Toxicological Review of Hexavalent Chromium" released in September 2010 for public comment, the EPA states that there is "evidence of an association between oral exposure to hexavalent chromium and stomach cancer in humans." Further, the report notes that "available evidence indicates that chromium interacts with DNA, resulting in DNA damage and mutagenesis."

Commercial TOC analyzers are used to measure the quantity of organic carbon present in a water sample, which is an indicator of water purity. Applications for TOC measurements include ultrapure water for pharmaceutical and electronics manufacturing, as well as municipal drinking water and wastewater and industrial wastewater from chemical and petrochemical plants, as examples.

Measurement of TOC relies on the conversion or oxidation of organic material in a water sample to $CO_2$, which can then be measured by conductivity, nondispersive Infrared (NDIR) detection, or attenuated total reflectance, as examples. Two common methods of oxidation include UV/Persulfate and high-temperature combustion. The UV/Persulfate method uses the combination of ultraviolet light and strong chemical oxidants, for example, sodium persulfate, to convert organic material to $CO_2$. High-temperature combustion uses thermal oxidation processes, often in the presence of catalysts, to convert the organic materials to $CO_2$. Both methods use an acid, for example, phosphoric acid, to initially remove "Total Inorganic Carbon" or TIC present in the water sample, as $CO_2$, prior to oxidation. Both of these methods suffer when the sample contains chlorides. With the UV/persulphate method, chloride interferes with the oxidation of the sample, resulting in under reading of the TOC. In the high-temperature method, chloride remains in the high-temperature reactor and, if not managed, can clog the reactor.

In TOC oxidative methods, an acid reagent is first added to convert the inorganic carbon in the sample having known volume (in the form of bicarbonate and carbonate anions) to gaseous $CO_2$. The $CO_2$ is removed by sparging the solution with a $CO_2$-free carrier gas, for example, $CO_2$-free nitrogen, to remove the liberated $CO_2$ which may then be measured as inorganic carbon (TIC). A chemical oxidant is then added to the resulting solution having known sample volume to oxidize the organic carbon present in the sample to a carbonate species and, in the case of UV/persulfate oxidation, generally with the aid of ultraviolet radiation. The $CO_2$ is again sparged from the solution using a $CO_2$-free gas, which may then be measured as organic carbon (TOC). The sum of the TIC and TOC yields the Total Carbon (TC) in the sample.

COD/TOC Analyses Using Ferrate Oxidation

An embodiment of an apparatus for analyzing total carbon and chemical oxygen demand in a sample, comprises: a first vial having an open end and a wall defining a first interior region, containing a first chosen quantity of an acid disposed in the first interior region into which the sample is introduced; means for introducing an inorganic base into the first interior region; means for introducing an oxidant into the first interior region; means for introducing an acid into the first interior region; a second vial having an open end and a wall defining a second interior region, containing a second chosen quantity of a pH-sensitive indicator disposed in the second interior region separate from the oxidant; and a separator comprising: a first sealing portion adapted for being sealed to the open end of the first vial and forming a fluid-tight seal therewith; an opposing second sealing portion adapted for being sealed to the open end of the second vial and forming a fluid-tight seal therewith; and a carbon dioxide permeable, liquid impermeable conduit disposed between the first sealing portion and the second sealing portion of the separator.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the inorganic base is chosen from bases comprising hydroxide ions.

The apparatus as described above, wherein the inorganic base is chosen from sodium hydroxide, lithium hydroxide, potassium hydroxide, and combinations thereof.

The apparatus as described above, wherein the oxidant comprises ferrate.

The apparatus as described above, wherein the source of ferrate comprises $[FeO4]2-/[HFeO4]-/[H2FeO4]/[H3FeO4]+$.

The apparatus as described above, wherein the pH-sensitive indicator changes color as a function of carbon dioxide present.

The apparatus as described above, wherein the indicator comprises thymol blue.

The apparatus as described above, further comprising an agitator for expelling carbon dioxide from the first vial.

The apparatus as described above, further comprising a photometer for measuring the absorbance of the pH-sensitive indicator in the second vial.

The apparatus as described above, further comprising a photometer for measuring the absorbance of the oxidant in said first vial.

Another embodiment of an apparatus for analyzing total carbon and chemical oxygen demand in a sample, includes: a first vial having an open end and a wall defining a first interior region, comprising: a first chosen quantity of an inorganic acid disposed in the first interior region into which the sample is introduced; a first hollow tube having a first open end and a second open end the first end being sealably attached to the wall of the first vial, and in fluid communication with the first interior region of the first vial, comprising: an oxidant disposed within the first hollow tube; a first compressible bulb sealably attached to the second end; a first breakable seal disposed between the first end of the first hollow tube and the interior region, responsive to the first compressible bulb, for preventing the oxidant from entering the first interior region until the first seal is broken; a second hollow tube having a first open end and a second open end the first end being sealably attached to the wall of the first vial, and in fluid communication with the first interior region of the first vial, comprising: an acid disposed within the second hollow tube; a second compressible bulb sealably attached to the second end; a second breakable seal disposed between the first end of said second hollow tube and the interior region, responsive to the first compressible bulb, for preventing the acid from entering the first interior region until the second seal is broken; and a third hollow tube having a first open end and a second open end the first end being sealably attached to the wall of the first vial, and in fluid communication with the interior portion of the first vial, comprising: an inorganic base disposed within the third hollow tube; a third compressible bulb sealably attached to the second end; a third breakable seal disposed between the first end of the third hollow tube and the interior region for preventing the inorganic base from entering the first interior region until the third seal is broken; a second vial an having an open end and a wall defining a second interior region containing a second chosen quantity of a pH-sensitive indicator disposed in the second interior region; and a separator comprising: a first sealing portion adapted for being sealed to the open end of the first vial and forming a fluid-tight seal therewith; an opposing second sealing portion adapted for being sealed to the open end of the second vial and forming a fluid-tight seal therewith; and a carbon dioxide permeable, liquid impermeable conduit disposed between the first sealing portion and the second sealing portion of the separator.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the inorganic base is chosen from bases including hydroxide ions.

The apparatus as described above, wherein the inorganic base is chosen from sodium hydroxide, potassium hydroxide, and combinations thereof.

The apparatus as described above, wherein the oxidant includes ferrate.

The apparatus as described above, wherein the source of ferrate includes $[FeO4]2-/[HFeO4]-/[H2FeO4]/[H3FeO4]+$.

The apparatus as described above, wherein the pH-sensitive indicator changes color as a function of carbon dioxide present.

The apparatus as described above, wherein the pH-sensitive indicator includes thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

Yet another embodiment of an apparatus for analyzing total carbon and chemical oxygen demand in a sample, comprises: a first vial having an open end and a wall defining a first interior region into which the sample is introduced; means for introducing an oxidant into the first interior region; means for introducing an acid into the first interior region; a second vial an having an open end and a wall defining a second interior region containing a second chosen quantity of a pH-sensitive indicator disposed in the second interior region; and a separator comprising: a first sealing portion adapted for being sealed to the open end of the first vial and forming a fluid-tight seal therewith; an opposing second sealing portion adapted for being sealed to the open end of the second vial and forming a fluid-tight seal therewith; and a carbon dioxide permeable, liquid impermeable conduit disposed between the first sealing portion and the second sealing portion of the separator.

The apparatus as described above, wherein the wall of the first vial is threaded in the region of the open end of said first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate includes $[FeO4]2-/[HFeO4]-/[H2FeO4]/[H3FeO4]+$.

The apparatus as described above, wherein the pH-sensitive indicator changes color as a function of carbon dioxide present.

The apparatus as described above, wherein the pH-sensitive indicator comprises thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

Still another embodiment of an apparatus for analyzing total carbon and chemical oxygen demand in a sample, comprises: a first vial having an open end and a wall defining a first interior region into which the sample is introduced; a second vial having an open end and a wall defining a second interior region containing a second chosen quantity of a pH-sensitive indicator disposed in the second interior region; and a separator comprising: a first sealing portion adapted for being sealed to the open end of the first vial and forming a fluid-tight seal therewith; an opposing second sealing portion adapted for being sealed to the open end of the second vial and forming a fluid-tight seal therewith; a carbon dioxide permeable, liquid impermeable conduit disposed between the first sealing portion and the second sealing portion of the separator; means for introducing an oxidant into the first interior region using the separator; and means for introducing an acid into the first interior region using the separator.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate includes $[FeO4]2-/[HFeO4]-/[H2FeO4]/[H3FeO4]+$.

The apparatus as described above, wherein the pH-sensitive indicator changes color as a function of carbon dioxide present.

The apparatus as described above, wherein the pH-sensitive indicator includes thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

Another embodiment of an apparatus for analyzing total carbon and chemical oxygen demand in a sample, comprises: a first vial having an open end and a wall defining a first interior region into which the sample is introduced; a second vial an having an open end and a wall defining a second interior region containing a second chosen quantity of a pH-sensitive indicator disposed in the second interior region; and a separator having a wall defining a third interior region, the wall having a first orifice comprising a first sealing member and a second orifice comprising a second sealing member, therein, comprising: a first sealing portion adapted for being sealed to the open end of the first vial and forming a fluid-tight seal therewith; an opposing second sealing portion adapted for being sealed to the open end of the second vial and forming a fluid-tight seal therewith; a carbon dioxide permeable, liquid impermeable conduit disposed between the first sealing portion and the second sealing portion of the separator; a first lever sealably movable through the first orifice; a first deformable container containing oxidant; a first tray disposed in the third interior region for holding the first deformable container, the first tray being attached to the first lever; a second lever sealably movable through the second orifice; a second deformable container containing acid; and a second tray disposed in the third interior region for holding the second deformable container, the first tray being attached to the first lever.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate includes [FeO4]2−/[HFeO4]−/[H2FeO4]/[H3FeO4]+.

The apparatus as described above, wherein the pH-sensitive indicator changes color as a function of carbon dioxide present.

The apparatus as described above, wherein the pH-sensitive indicator includes thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

Yet another embodiment of an apparatus for analyzing total carbon and chemical oxygen demand in a sample, comprises: a first vial having an open end and a wall defining a first interior region into which the sample is introduced; a second vial an having an open end and a wall defining a second interior region containing a second chosen quantity of a pH-sensitive indicator disposed in the second interior region; and a separator having a wall defining a third interior region, the wall having an orifice comprising a sealing member therein, comprising: a first sealing portion adapted for being sealed to the open end of the first vial and forming a fluid-tight seal therewith; an opposing second sealing portion adapted for being sealed to the open end of the second vial and forming a fluid-tight seal therewith; a carbon dioxide permeable, liquid impermeable conduit disposed between the first sealing portion and the second sealing portion of the separator; a lever sealably movable through the orifice and forming a piston in the third interior region; a hollow tube having a first open end and a second open end, disposed in the third interior region and adapted for movably receiving the piston into the first end thereof; a first deformable container having a first seal and containing oxidant, the first deformable container disposed in the hollow portion of the tube in the vicinity of the second end thereof; and a second deformable container having a second seal and containing an acid, the second deformable container being disposed in the hollow portion of the tube in the region of the first end thereof, and spaced apart from the first deformable container.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate includes [FeO4]2−/[HFeO4]−/[H2FeO4]/[H3FeO4]+.

The apparatus as described above, wherein the pH-sensitive indicator changes color as a function of carbon dioxide present.

The apparatus as described above, wherein the pH-sensitive indicator includes thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further comprising a photometer for measuring the absorbance of the oxidant in the first vial.

Still another embodiment of an apparatus for analyzing total organic carbon and chemical oxygen demand in a sample, comprises: a first vial having an open end and a wall defining a first interior region into which the sample and an oxidant are introduced; a second vial an having an open end and a wall defining a second interior region containing a second chosen quantity of a pH-sensitive indicator disposed in the second interior region; and a separator comprising: a first sealing portion adapted for being sealed to the open end of the first vial and forming a fluid-tight seal therewith; an opposing second sealing portion adapted for being sealed to the open end of the second vial and forming a fluid-tight seal therewith; a carbon dioxide permeable, liquid impermeable conduit disposed between the first sealing portion and the second sealing portion of the separator; and means for introducing an acid into the first interior region.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate includes [FeO4]2−/[HFeO4]−/[H2FeO4]/[H3FeO4]+.

The apparatus as described above, wherein the pH-sensitive indicator changes color as a function of carbon dioxide present.

The apparatus as described above, wherein the pH-sensitive indicator includes thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

Another embodiment of an apparatus for analyzing total organic carbon and chemical oxygen demand in a sample, comprises: a first vial having an open end and a wall defining a first interior region into which the sample and an oxidant are introduced; a second vial an having an open end and a wall defining a second interior region containing a second chosen quantity of a pH-sensitive indicator disposed in the second interior region; and a separator having a wall defining a third interior region comprising: a first sealing portion adapted for being sealed to the open end of the first vial and forming a fluid-tight seal therewith; an opposing second sealing portion adapted for being sealed to the open end of the second vial and forming a fluid-tight seal therewith; a carbon dioxide permeable, liquid impermeable conduit disposed between the first sealing portion and the second sealing portion of the separator; and a container having a seal for holding an acid disposed in the third interior region on the side of the conduit of the first sealing portion of the separator.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate comprises [FeO4]2−/[HFeO4]−/[H2FeO4]/[H3FeO4]+.

The apparatus as described above, wherein the pH-sensitive indicator changes color as a function of carbon dioxide present.

The apparatus as described above, wherein the pH-sensitive indicator includes thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

Yet another embodiment of an apparatus for analyzing total carbon and chemical oxygen demand in a sample, comprises: a first vial having an open end and a wall having an outer surface and defining a first interior region, comprising: a first chosen quantity of an inorganic base disposed in the first interior region into which the sample is introduced; a first hollow tube having a first open end comprising a sealing member and a second open end comprising a sealing member, the first end being sealably attached to the wall of the first vial; a second hollow tube having a first open end comprising a sealing member and a second open end comprising a sealing member, the first end being sealably attached to the wall of the first vial, the first end of the second hollow tube being disposed opposite to the first end of the first hollow tube on the outer surface of the wall of the first vial; and a cylindrical rod adapted to sealably move through the first hollow tube and the second hollow tube, the rod having a first detent effective for holding oxidant within the first hollow tube outside of the wall of the first vial, and a second detent effective for holding acid within the second hollow tube outside of the wall of the first vial; a second vial an having an open end and a wall defining a second interior region containing a second chosen quantity of a pH-sensitive indicator disposed in the second interior region; and a separator comprising: a first sealing portion adapted for being sealed to the open end of the first vial and forming a fluid-tight seal therewith; an opposing second sealing portion adapted for being sealed to the open end of the second vial and forming a fluid-tight seal therewith; and a carbon dioxide permeable, liquid impermeable conduit disposed between the first sealing portion and the second sealing portion of the separator.

The apparatus as described above, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

The apparatus as described above, wherein the acid is chosen from phosphoric acid, sulfuric acid, nitric acid, and hydrochloric acid.

The apparatus as described above, wherein the oxidant includes ferrate.

The apparatus as described above, wherein the source of ferrate comprises [FeO4]2−/[HFeO4]−/[2FeO4]/[H3FeO4]+.

The apparatus as described above, wherein the pH-sensitive indicator changes color as a function of carbon dioxide present.

The apparatus as described above, wherein the pH-sensitive indicator comprises thymol blue.

The apparatus as described above, further including an agitator for expelling carbon dioxide from the first vial.

The apparatus as described above, further including a photometer for measuring the absorbance of the pH-sensitive indicator in the second vial.

The apparatus as described above, further including a photometer for measuring the absorbance of the oxidant in the first vial.

An embodiment of a method for analyzing carbon and chemical oxygen demand in the same sample, comprises the steps of: adding a first acid to the sample to lower the pH of said sample to a pH less than about 4; removing carbon dioxide generated from inorganic carbon present in the sample; adjusting the sample pH to a chosen pH value; providing sufficient ferrate to the sample previously adjusted to the chosen pH for a sufficient period of time to oxidize the organic carbon therein; determining the chemical oxygen demand using the change in absorbance of the sample containing ferrate, after the step of oxidation of the organic carbon; liberating the carbon dioxide formed in the step of oxidation of the organic carbon by acidifying the sample with a second acid to a pH of less than about 4; collecting the carbon dioxide generated from the step of acidifying the sample with a second acid; and measuring the carbon dioxide collected in the step of collecting the carbon dioxide generated from the step of acidifying the sample with a second acid; whereby measurement of the total organic carbon present in the sample is obtained.

The method as described above, wherein the first acid and the second acid are chosen from phosphoric acid, sulfuric acid, nitric acid, and hydrochloric acid.

The method as described above, wherein the step of removing the carbon dioxide comprises agitating the sample.

The method as described above, wherein the chosen pH value is between about 6 and about 12.

The method as described above, wherein the step of measuring the carbon dioxide comprises dissolving the carbon dioxide in a solution containing thymol blue, and measuring the absorption of the resulting solution.

The method as described above, wherein the step of providing sufficient ferrate to the sample for a sufficient period of time to oxidize the organic carbon therein, includes adding [FeO4]2− to the sample.

The method as described above, further comprising the step of measuring the rate of change of absorption of the sample containing ferrate to determine oxidation termination.

The method as described above, further comprising the step of measuring the rate of change of absorption of the solution of thymol blue to determine oxidation termination.

The method as described above, further comprising the step of measuring the carbon dioxide generated from inorganic carbon present in the sample, whereby a measurement of total carbon in the sample is obtained.

The apparatus as described above, wherein the acid is chosen from phosphoric acid, sulfuric acid, nitric acid, and hydrochloric acid.

The apparatus as described above, wherein the inorganic base is chosen from bases comprising hydroxide ions.

The apparatus as described above, wherein the oxidant comprises ferrate.

The apparatus as described above, wherein the oxidant comprises ferrate and a source of ferrate comprises [FeO4]2-/[HFeO4]-/[H2FeO4]/[H3FeO4]+.

The apparatus as described above, wherein the pH-sensitive indicator changes color as a function of carbon dioxide present.

The apparatus as described above, wherein the pH-sensitive indicator comprises thymol blue.

The apparatus as described above, further comprising an agitator for expelling carbon dioxide from the first vial.

The apparatus as described above, further comprising a photometer for measuring the absorbance of the pH-sensitive indicator in the second vial.

The apparatus as described above, further comprising a photometer for measuring the absorbance of the oxidant in said first vial.

BRIEF DESCRIPTION OF THE DRAWINGS

In the drawings:

FIG. 6a is a schematic representation of a side view of the assembled measurement apparatus illustrating the separator being sealably attached to oxidation vial after its cap is removed, and indicator vial, containing a pH sensitive indicator being sealably attached to the separator, such that the liquids are confined to the vials, while carbon dioxide may freely pass through the separator from the oxidation vial to the indicator vial, and ferrate being introduced into oxidation vial by compressing another of the tubes.

FIG. 6b is a schematic representation of a side view of the assembled measurement apparatus shown in FIG. 6a showing the reacted ferrate in the oxidation/detection vial ready for analysis using the spectrophotometer.

FIG. 6c shows the spectrophotometer.

FIG. 7a is a schematic representation of a side view of the assembled apparatus illustrating the addition of acid to the oxidation vial by compressing another of the tubes for releasing carbon dioxide generated by the oxidation of the organic carbon in the sample by ferrate, wherein the carbon dioxide freely passes through the separator into the indicator vial and changes the pH of the pH sensitive indicator therein.

FIG. 7b shows the apparatus shown in FIG. 7a inverted so that the change of absorption of the pH-sensitive indicator in the detection vial may be measured using the spectrophotometer.

FIG. 7c shows the spectrophotometer.

DETAILED DESCRIPTION

Figure 1:
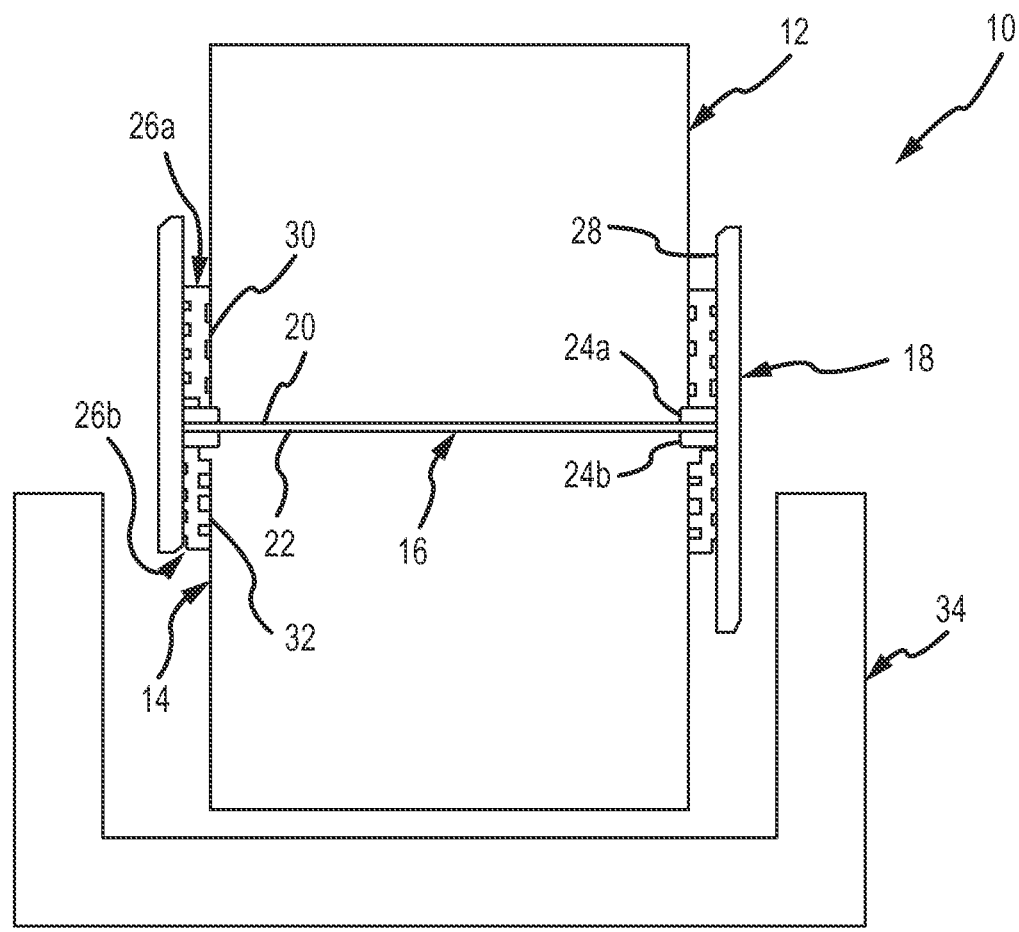
FIG. 1 is a schematic representation of an embodiment of the apparatus for determining COD and TOC of the same aqueous sample, illustrating a reaction or oxidation vial, an indicator vial, and a separator for sealably supporting a carbon dioxide permeable, liquid impermeable conduit between the open ends of the oxidation vial and the indicator vial.

As used herein, the term "ferrate" means iron in a valence state greater than zero, including +1, +2, +3, +4, +5, and +6, unless the context clearly dictates otherwise.

As used herein, the term "high valence iron species" means those valences of the element iron that are greater than 3, that is, $Fe^{4+}$ (Fe(IV)), $Fe^{5+}$ (Fe(V)) and $Fe^{6+}$ (Fe(VI)). Iron in the lower valences 0-3 can be oxidized to the higher valences that have sufficient oxidation potential to oxidize organic compounds found in the environment. For example, oxidants such as ozone, hypochlorous acid and hydrogen peroxide, amongst others, are used to oxidize the lower valences of iron to the higher valences.

Briefly, embodiments disclosed herein include apparatuses and methods for measurement of any or all of the Total Organic Carbon (TOC), Total Inorganic Carbon (TIC), Total Carbon (TC), and nitrogenous and carbonaceous Chemical Oxygen Demand (COD) in the same aqueous sample using higher valence iron compositions as oxidants. An apparatus for analyzing total carbon and chemical oxygen demand in a sample may include a first vial into which the sample is introduced, and means for introducing an inorganic base, a colored oxidant, and at least one chosen quantity of acid into the first vial at chosen times during the analysis; a second vial containing a second chosen quantity of a pH sensitive colored indicator; a separator adapted for being sealed to the open end of the first vial and to the open end of said second vial; and a carbon dioxide permeable, liquid impermeable conduit disposed in the separator for permitting carbon dioxide to pass from the first vial to the second vial. As an example, a $CO_2$ permeable membrane, like Gore-Tex®, a fluoro-plastic membrane of stretched polytetrafluoroethylene (PTFE) sheet, which can be heat sealed, thermo-formed, vacuum formed, heat bonded, welded, metallized, laminated, or combined with other materials may be used for the conduit. A hollow tube having a valve connecting the first and second vials may also serve as a conduit.

Means for measuring the absorption of the colored oxidant to determine its initial and final concentrations, and means for measuring the absorption of the pH sensitive colored indicator in the second vial for determining the quantity of carbon dioxide generated in the first vial, are also provided. The headspace volume in the first vial will fill with $CO_2$ once the ferrate-oxidized sample is acidified. Once there is positive pressure in the first vial the $CO_2$ will permeate through the permeable membrane (conduit) to the second vial where it changes the indicator's color until equilibrium is attained between the first vial and the second vial. The difference between the initial and the final absorbance of the indicator along with the quantity of the $CO_2$ calculated to remain in the head space of the first vial after equilibration is used to quantify the $CO_2$. Moreover, in the situation where thymol blue is used as the indicator, the second vial will be basic, and $CO_2$ passing through the conduit will be irreversibly converted into $HCO_3^-$ and $CO_3^{2-}$, which will shift the equilibrium between the $CO_2$ concentration in the first and second vials. This enables the complete transfer of $CO_2$ from the first vial to the second vial which would then be quantified using the color change in the indicator.

The separator may be screwed onto a threaded portion at the open end of the first vial and onto a threaded portion at the open end of the second vial. This provides a straight-forward assembly procedure for the apparatus once the initial reagents and sample are added to the vials.

In use, the sample is added to the first vial either before or after a first sample of acid is added to thereto for lowering the pH of the sample to less than about 4. If the quantity of carbon dioxide released from the inorganic carbon present in the sample is to be measured, the apparatus is assembled and the carbon dioxide permitted to enter the second vial for measurement. If a measurement of the inorganic carbon in the sample is not intended, the apparatus may be assembled after the carbon dioxide is liberated to the atmosphere. As stated above, means may be provided for adding the acid to the first vial after the apparatus is assembled. The sample is then made more basic by adding an inorganic base. In some situations the pH is adjusted to optimize the oxidation of the carbon compositions in the sample by the colored oxidant. The precise pH will depend upon the nature of the organic carbon contents to be oxidized. The chosen pH value is typically between about 6 and about 12. It is known that for acidic pH values (below about 6) the kinetics and thermodynamics of ferrate oxidization is preferably towards the oxidation of water and the production of oxygen. As the pH is increased, a transition occurs where ferrate oxidation of organics begins (generally between about pH 6 to about pH 9). At above about pH 9, ferrate preferentially oxidizes organics as opposed to water.

Sufficient colored oxidant, ferrate, as an example, is added to the sample, and a sufficient period of time is permitted for the oxidation of the organic carbon therein. The chemical oxygen demand is determined by measuring the change in absorbance of the sample containing the colored oxidant, after the organic carbon is oxidized. Aqueous solutions of ferrates are pink when dilute, and deep red or purple at higher concentrations. The carbon dioxide generated from oxidation of the organic carbon is released from the sample by acidifying the sample with a second acid to a pH of less than about 4, and passes through the conduit into the second vial containing a pH sensitive indicator. A useful pH sensitive indicator includes thymol blue. The carbon dioxide entering the second vial changes the pH of the solution contacting the indicator, which may then be measured by changes in light absorption. The apparatus may be agitated for about 15 min. in order to assist in the release of carbon dioxide after the sample is acidified to ensure all of the $CO_2$ has been released.

The first acid and the second acid may be chosen from phosphoric acid, sulfuric acid, nitric acid, and hydrochloric acid. Although inorganic acids are preferred, if an organic acid is chosen, the oxidant concentration measurements used for the COD determination will have to be corrected for the additional oxidant expended in oxidizing the additional carbon-containing moieties. Inorganic bases are chosen from bases comprising hydroxide ions, such as lithium hydroxide, sodium hydroxide and potassium hydroxide, and combinations thereof.

Ferrate oxidant is added to the sample as the salt of an alkali metal, such as $Na_2FeO_4$ (sodium ferrate) and $K_2FeO_4$ (potassium ferrate), as examples. Oxidation using ferrate does not oxidize chloride ions and hence is not affected by the presence of chloride during organic compound oxidation processes. Ferrate anion is unstable at neutral or acidic pH values, decomposing to iron(III):

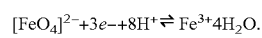
$$[FeO_4]^{2-} + 3e^- + 8H^+ \rightleftharpoons Fe^{3+} + 4H_2O.$$

The reduction goes through intermediate species in which iron has oxidation states +5 and +4 (See. e.g., Egon Wiberg; Nils Wiberg; Arnold Frederick Holleman (2001), *Inorganic chemistry*, Academic Press, pp. 1457-1458). These anions are more reactive than Fe(VI) (See, e.g., Gary M. Brittenham (1994), Raymond J. Bergeron, ed., *The Development of Iron Chelators for Clinical Use*, CRC Press, pp. 37-38). In alkaline conditions, ferrates are more stable, lasting for about 5 h to about 50 h at pH≥9. Id. As a result, the ferrate salt is kept dry in storage.

The baseline light absorbance is measured at a wavelength diagnostic of ferrate ion, one candidate wavelength being 504 nm, although others within the range of about 500 to about 515 nm may also be operable. This "blank" measurement may be performed by mixing the same amount of ferrate into the same volume of pure water as the sample volume, then measuring the absorbance to obtain a baseline absorbance. Measurement of the light absorbance of a sample and subtracting the baseline absorbance provides the net absorbance due only to the COD of the sample, and permits the determination of the COD of the sample by reference to a calibration table.

Lihong Li et al. in Analytical Chemical Acta, 754, pages 47-53 (19 Nov. 2012), describe the limitation of dichromate COD measurements as an inability to oxidize nitrogenous organic compounds. Such compounds are persistent compounds that cannot be completely oxidized by dichromate in strong acid and high temperatures. Thus, the nitrogenous biological oxygen demand (NBOD) is not accurately measured by dichromate COD. Since ferrate oxidizes nitrogenous compounds more efficiently than dichromate, the NBOD determined using ferrate will be more accurate than dichromate COD.

Reference will now be made in detail to the present embodiments, examples of which are illustrated in the accompanying drawings. In the FIGURES, similar structure will be identified using identical reference characters. It will be understood that the FIGURES are for the purpose of describing particular embodiments and are not intended as limiting. Turning now to FIG. 1, illustrated is a schematic representation of an embodiment of apparatus, 10, for determining COD and TOC of the same aqueous sample. Reaction or oxidation vial, 12, (first vial), and detection vial, 14, (second vial), separated by $CO_2$-permeable, liquid impermeable conduit or membrane, 16, are joined by separator, 18, which provides a liquid and gas seal between conduit 16 and the open ends of vials 12 and 14. One embodiment of separator 18 is a membrane double cap sold in the LCK 385 TOC cuvette test, available from Hach Lange GmbH, Dusseldorf, Germany. Vials 12 and 14 may be cylindrical having open ends, 20, and, 22, respectively. As will be discussed below, vials 12 and 14 are fabricated from acid and base proof, transparent materials, PTFE lined caps with polypropylene backing. Shown in FIG. 1 are supports/seals, 24a, and, 24b, for sealing conduit 16 to separator 18, and to the open ends of vials 12 and 14. Shown also are female threaded portions, 26a, and, 26b, on the inner surface, 28, of separator 18, adapted for receiving threaded portions, 30, and, 32, on the outer surface of vials 12 and 14, respectively, in the vicinity of the open ends thereof. Although other means for sealing vials 12 and 14 to separator 18 and conduit 16 may be anticipated, the mating threaded portions permit straightforward assembly and disassembly of apparatus 10. Spectrophotometer, 34, is adapted to receive either vial 12 or vial 14 for measuring the absorption of liquids present therein, and changes in absorption thereof.

As will be discussed hereinbelow, and not shown in FIG. 1, means are provided for introducing reagents in a prescribed order into vials 12 and 14 after apparatus 10 is assembled and sealed. Embodiments will be described for introducing the reagents through the separator and through the vials.

In one embodiment, a sample to be analyzed is introduced into oxidant vial 12 along with a quantity of acid effective for adjusting the pH of the sample to less than or equal to 4. Carbon dioxide released from any inorganic carbon in the sample is permitted to escape from oxidant vial 12 through its open end, before it is attached to separator 18. Vial 12 may be agitated, ultrasound applied thereto, or heated to a temperature such that the organic materials are not oxidized, or a combination of these steps, to assist in the complete removal of the carbon dioxide from the sample. As examples, the apparatus may be agitated for about 15 min., or heated to less than about 70° C. and agitated for about 10 min., in order to assist in the release of carbon dioxide after the sample is acidified. It should be mentioned that the temperature limitation is important, since it would be undesirable to oxidize the organic carbon species at this time. An inorganic base, such as LiOH, NaOH or KOH, is added to the vial after the carbon dioxide is removed. As stated hereinabove, ferrate oxidant is stabilized in solution at higher pH values. Potassium, sodium or lithium ferrate is then added to the basified sample. The COD of the sample may now be determined from the change in absorption measured of the solution resulting from a quantity of the ferrate having reacted with the sample using spectrophotometer 34. That is, the difference in the absorption intensity between the sample containing the initial ferrate concentration and that after reaction with the sample is used to determine the COD.

Figure 2:
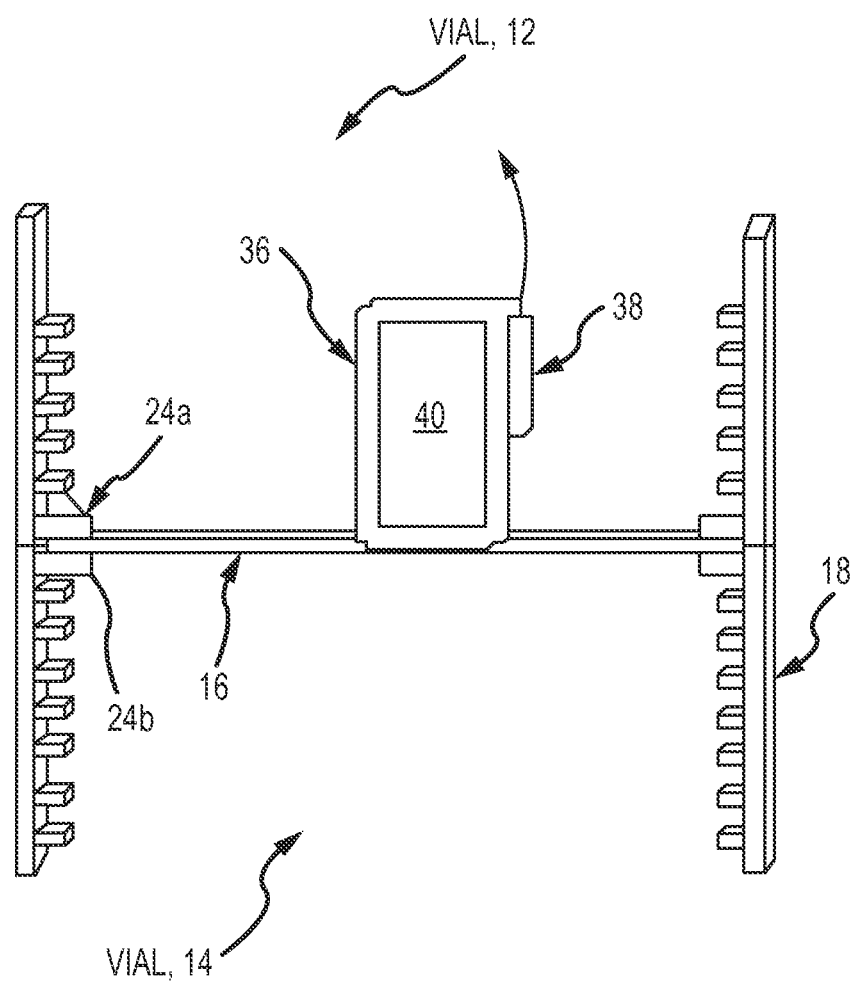
FIG. 2 is a schematic representation of a side view of the embodiment of the separator shown in FIG. 1, illustrating a container for holding a solid acid mounted on the conduit on the side thereof of the oxidant vial and having an opening sealed using an inert foil, for containing a solid acid.

If COD and TOC are being measured and not TIC, FIG. 2 is a schematic representation of a side view of an embodiment of separator 18 wherein only one reagent is required to be added to sealed apparatus 10. Shown in FIG. 2 is container, 36, attached to conduit 16 on the side thereof where vial 12 (FIG. 3) is seated, having removable inert foil seal, 38, for containing solid acid, 40.

Figure 3:
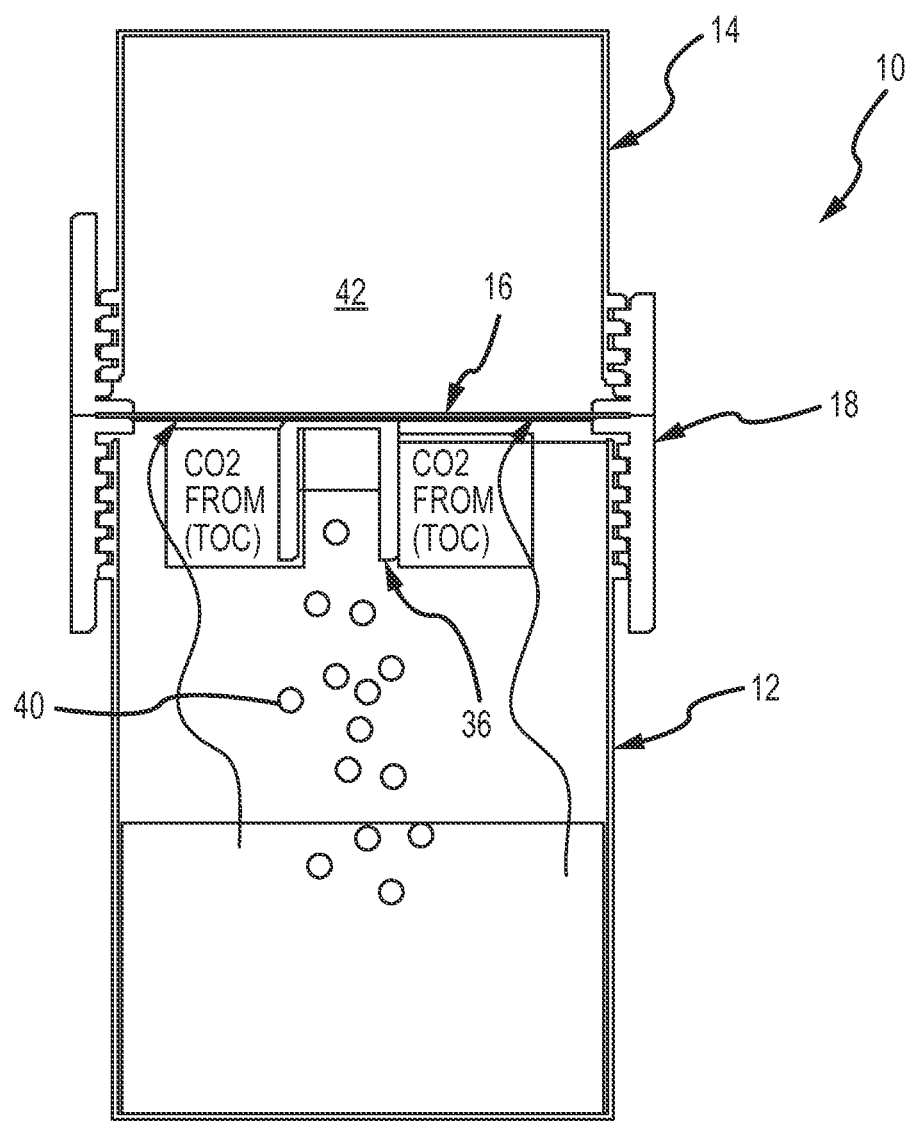
FIG. 3 is a schematic representation of a side view of the sealed apparatus, wherein a pH sensitive indicator is placed in the indicator vial, and the solid acid contained in the container illustrated in FIG. 2, is introduced into the oxidant vial containing a basified sample/ferrate solution, thereby releasing carbon dioxide generated by the ferrate oxidation of organic carbon in the sample into the indicator vial.

Turning to FIG. 3, sample indicator vial 14, into which a quantity of a pH sensitive indicator, 42, such as thymol blue, is attached to separator 18 on the side of conduit 16 opposite to container 36. First, ferrate is added to a basified sample. After the ferrate has reacted with the organic carbon in the sample, and the COD is determined by measuring the change in absorbance of the ferrate oxidant, sealing foil 38 is removed from container 36, vial 12 is attached to separator 18, and apparatus 10 is inverted to permit solid acid 40 to enter the basified sample/ferrate solution, thereby releasing carbon dioxide generated by the oxidation of the organic carbon in the solution by ferrate. It should be mentioned that loss of carbon dioxide is minimal from the basic solution. Apparatus 10 may be agitated or ultrasound applied thereto to assist in the removal of carbon dioxide from the sample. Released carbon dioxide passes through conduit 16 into indicator solution 42, the absorbance thereof being measured using spectrophotometer 34, whereby the sample TOC is determined. A wavelength of about 435 nm may be used for the thymol blue absorbance measurements.

Figure 4:
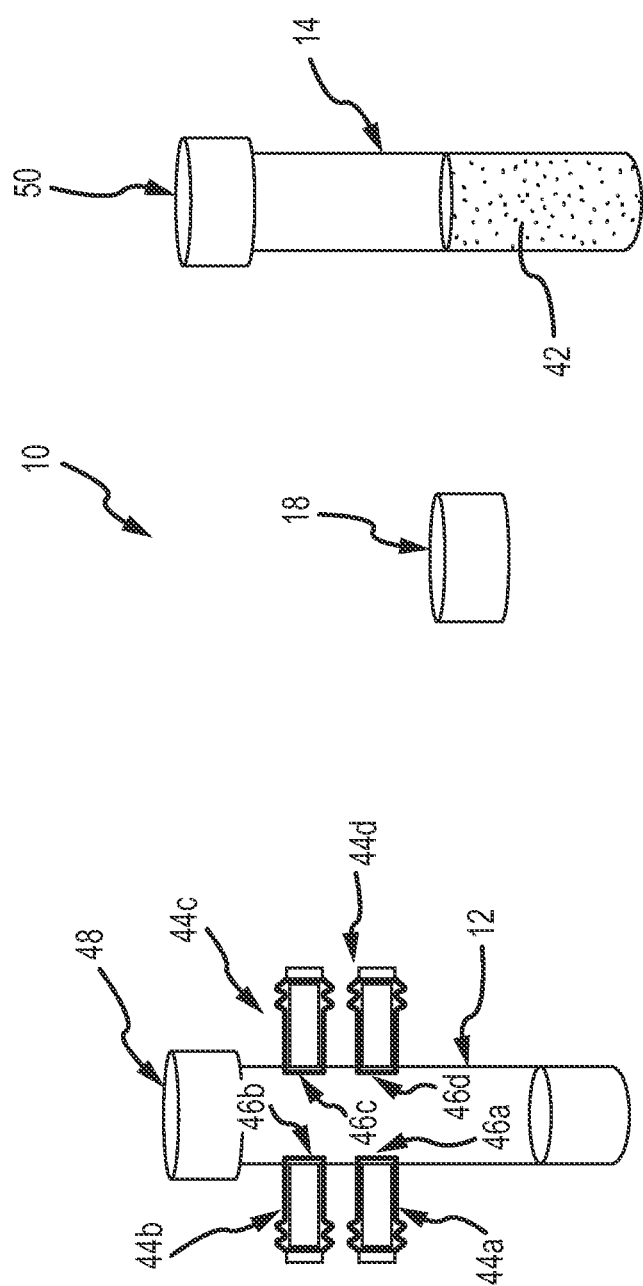
FIG. 4 is a schematic representation of a side view of an embodiment of the apparatus for measuring COD and TOC of the same sample, or measuring COD, TOC, TIC and TC of the same sample, illustrating at least three compressible tubular arms for delivering reagents through inert seals in the oxidation vial.

FIG. 4 is a schematic representation of a side view of an embodiment of the apparatus wherein several reagents may be directly added to oxidation vial, 12, illustrating at least three compressible tubular arms, 44a-44d, for delivering reagents through inert seals, 46a-46d, respectively, into oxidation vial 12. Apparatus 10 may be utilized for measuring COD and TOC of the same sample, or measuring COD, TOC, TIC and TC of the same sample. Flexible compositions of Polyether ether ketone and Teflon, as examples, may be used to fabricate tubes 44a-44d, while the inert seals may be fabricated from PTFE, and other fluorinated polymers. Compressing tubes 44a-44d opens inert seals 46a-46d, respectively, and permits the reagents to enter vial 12. Reagents may include ferrate oxidant, at least one acid, and a base/buffer agent.

In another embodiment of apparatus 10 of FIG. 4, incompressible glass tubes may replace the flexible tubular arms 44a-44d, and the force required to release seals 46a-46d, may be applied using compressible bulbs at the open end of each tube (Not shown in FIG. 4). Apparatus 10 further includes separator/membrane 18/16, and detection vial 14 containing pH sensitive indicator 42, such as thymol blue, and sealed by cap, 50.

Figure 5:
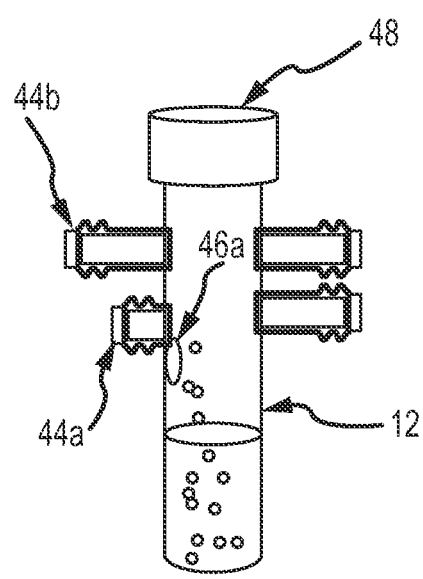
FIG. 5, is a schematic representation of one of the tubular arms of the oxidation tube being compressed to introduce a basic reagent into the sample.

A user removes cap, 48, from vial 12 and adds a quantity of aqueous sample and an acid into vial 12, thereby generating carbon dioxide from the inorganic carbon present in the sample. Vial 12 may be agitated, ultrasonic energy applied thereto, or heated, or a combination thereof, combined with sparging with a CCVfree gas, such that carbon dioxide generated from the inorganic carbon in the sample is more completely released from the sample. As may be observed from FIG. 5, after expelling the carbon dioxide, cap 48 is replaced, and tube 44a is compressed to introduce an inorganic base into vial 12 to basify the sample for stabilizing the ferrate oxidant and increasing its oxidation efficiency. Vial 12 may be shaken to mix the base/buffer reagent with the sample.

FIG. 6a is a schematic representation of a side view of the assembled measurement apparatus 10, illustrating separator 18 being sealably attached to vial 12 after cap 48 is removed, and vial 14, containing pH-sensitive indicator 42 being sealably attached to separator 18, such that the liquids are confined to vial 12 and vial 14, while carbon dioxide may freely pass through conduit 16 (not shown in FIG. 6) in separator 18 from vial 12 to vial 14, and ferrate being introduced into vial 12 by compressing tube 44d. FIG. 6b is a schematic representation of a side view of the assembled measurement apparatus 10, showing the reacted ferrate in vial 12 ready for analysis. As discussed hereinabove, the COD of the sample may be determined by measuring the change of absorption of the ferrate oxidizer in vial 12 using spectrophotometer 34, shown in FIG. 6c.

FIG. 7a illustrates the addition of acid to vial 12 by compressing tube 44b for releasing carbon dioxide generated by the oxidation of the organic carbon in the sample by ferrate, wherein the carbon dioxide freely passes through membrane 16 (not shown in FIG. 7a) in separator 18 into vial 14 and changes the pH of the pH-sensitive indicator 42 therein. As shown in FIG. 7b, apparatus 10 may now be inverted so that, as discussed hereinabove, the change of absorption of pH-sensitive indicator 42 may be measured using spectrophotometer 34, illustrated in FIG. 7c, to determine the quantity of carbon dioxide generated by oxidation of the organic carbon in the sample, from which the TOC is determined.

In the situation where the total carbon is to be measured, the carbon dioxide generated from the inorganic carbon in the sample by acidification of the sample, in this situation, using another compressible tube to introduce the acid into oxidation vial 12 of an assembled apparatus 10, would be permitted to pass through conduit 16 into a second indicator vial 14 containing a pH sensitive indicator 42 instead of permitting the carbon dioxide to escape into the atmosphere. The change in absorption of the pH sensitive indicator is used to determine the quantity of carbon dioxide generated from the inorganic carbon present in the sample, as discussed hereinabove.

Figure 8:
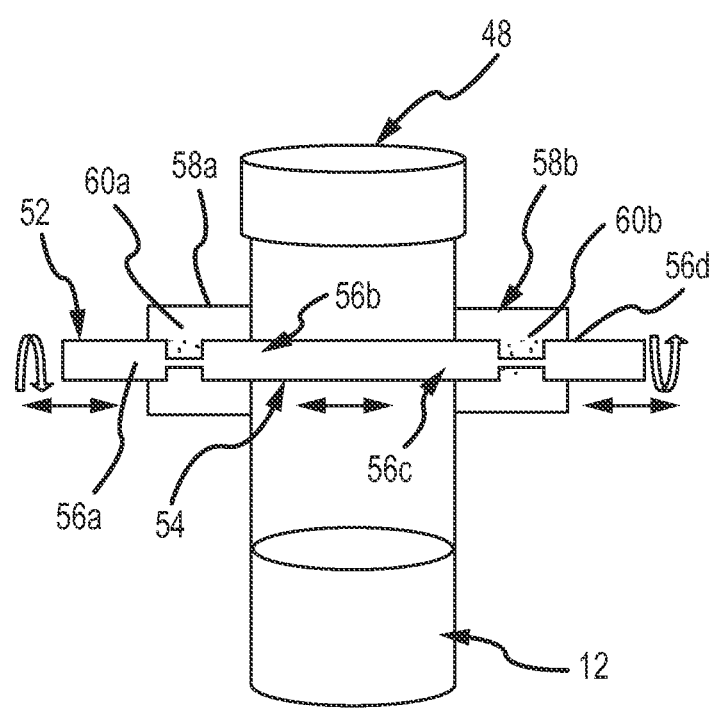
FIG. 8 is a schematic representation of another embodiment of the apparatus for introducing reagents into the oxidation vial, which contains a basified sample, the carbon dioxide from the inorganic carbon in the sample having already been released to the atmosphere, illustrating a rod which slidably passes through seals in the oxidation vial, and seals in chambers sealed to the outer surface of the oxidation vial, detents in the rod containing solid acid and solid ferrate reagents immobilized therein, which may be introduced into a sample in the oxidation vial by pushing the rod in one direction or the other such that either detent is within the oxidation vial.

FIG. 8 is a schematic representation of another embodiment of the apparatus for introducing reagents directly into oxidation vial 12, which contains a basified sample, the carbon dioxide from the inorganic carbon in the sample having already been released to the atmosphere. Shown is rod, 52, having a portion, 54, which slidably passes through seals, 56b, and, 56c, in vial 12, and seals, 56a, and, 56d, in chambers, 58a, and, 58b, which are sealed to the outer surface of vial 12. Detents, 60a, and, 60b, in rod 52 contain either a solid acid or solid ferrate reagent immobilized therein, which may be introduced into a sample in vial 12 by pushing rod 52 in one direction or the other such that one of the detents is within vial 12, and shaking vial 12 to dissolve the reagent.

Figure 9:
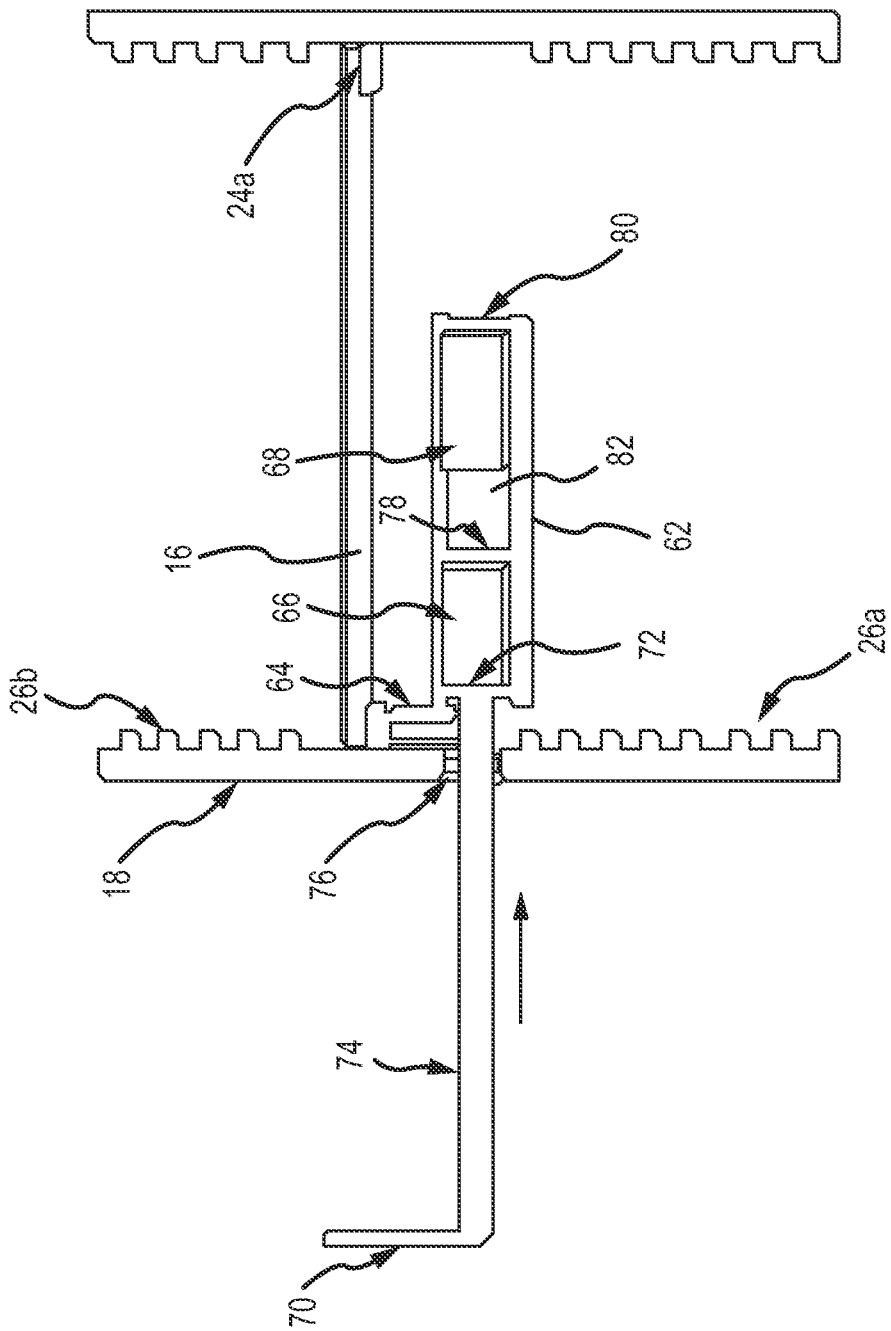
FIG. 9 is a schematic representation of a side view of an embodiment of the apparatus illustrating the addition of two reagents by the action of a lever attached to the separator onto which the oxidation/detection vial and the detection vial are attached.

FIG. 9 is a schematic representation of a side view of an embodiment of the apparatus illustrating the addition of two reagents using separator 18 onto which vials 12 and 14, not shown in FIG. 9, are attached using threads 26a and 26b, respectively. Cylinder, 62, supported on the inside of separator 18 on block, 64, contains inert, flexible bags, 66, and, 68, containing acid and ferrate, respectively. Materials such as Teflon lined polyester, for example, may be used. Lever, 70, terminating in piston, 72, having shank, 74, adapted to slidably move through seal, 76, contacts bag 66. Seal 76, which may include at least one Teflon-coated O-ring, provides a gas seal for separator 18. Bags 66 and 68 are sealed using inert foils, 78, and, 80, respectively, and are separated by air space, 82. When ferrate is to be added to vial 12, lever 70 is pushed inward such that piston 72 moves bag 66 forward, compressing the air in space 82 and forcing foil 80 to be dislodged, bag 66 spilling its contents into vial 12, seal 78 remaining in place. When acid is to be added to vial 12, lever 70 is pushed further into cylinder 62 until foil 78 reaches the end of cylinder 62 and is dislodged from bag 66.

Figure 10:
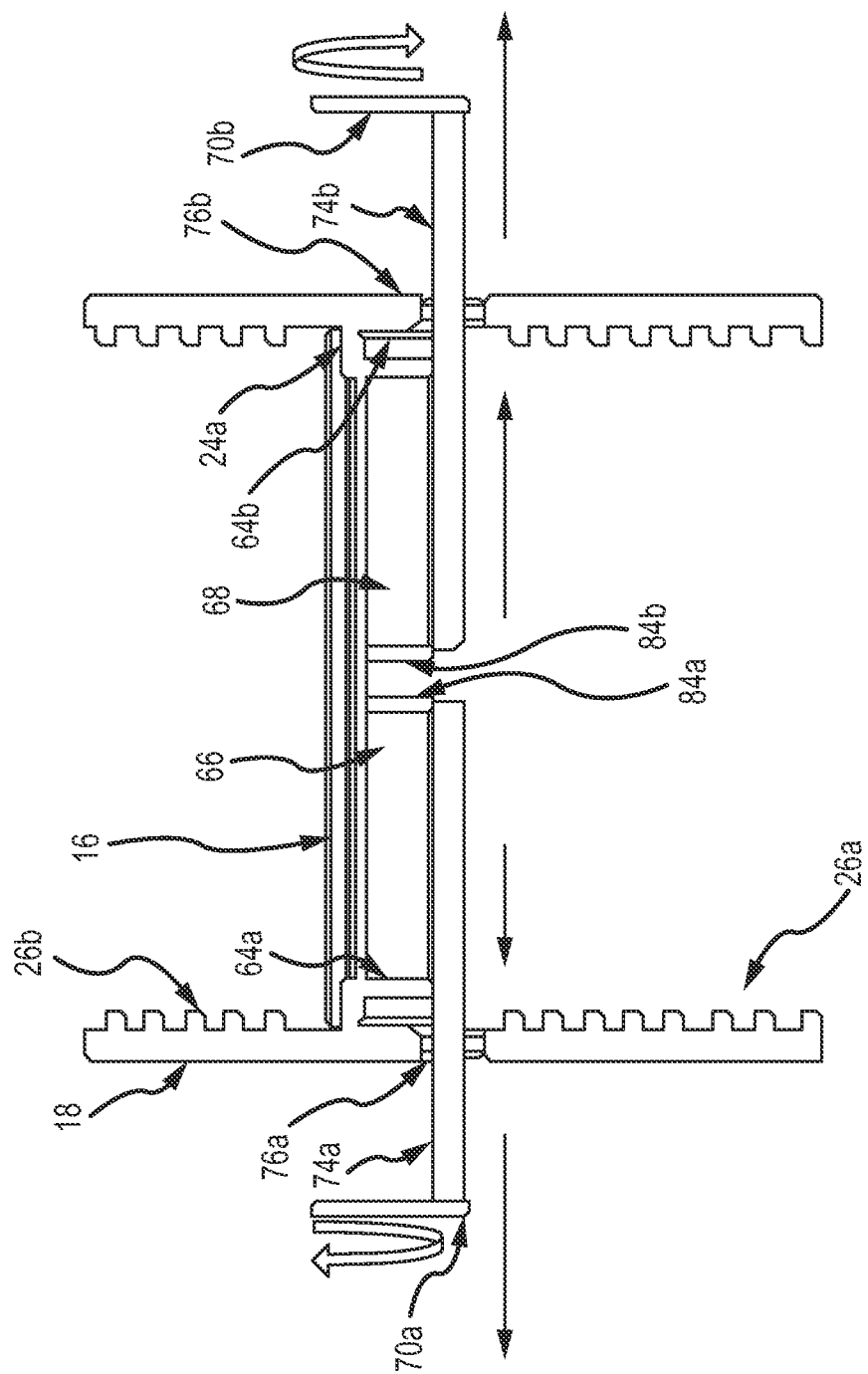
FIG. 10 is a schematic representation of a side view of another embodiment of the apparatus for adding reagents by the action of two levers attached to the separator onto which the oxidation/detection vial and the detection vial are attached.
Figure 11:
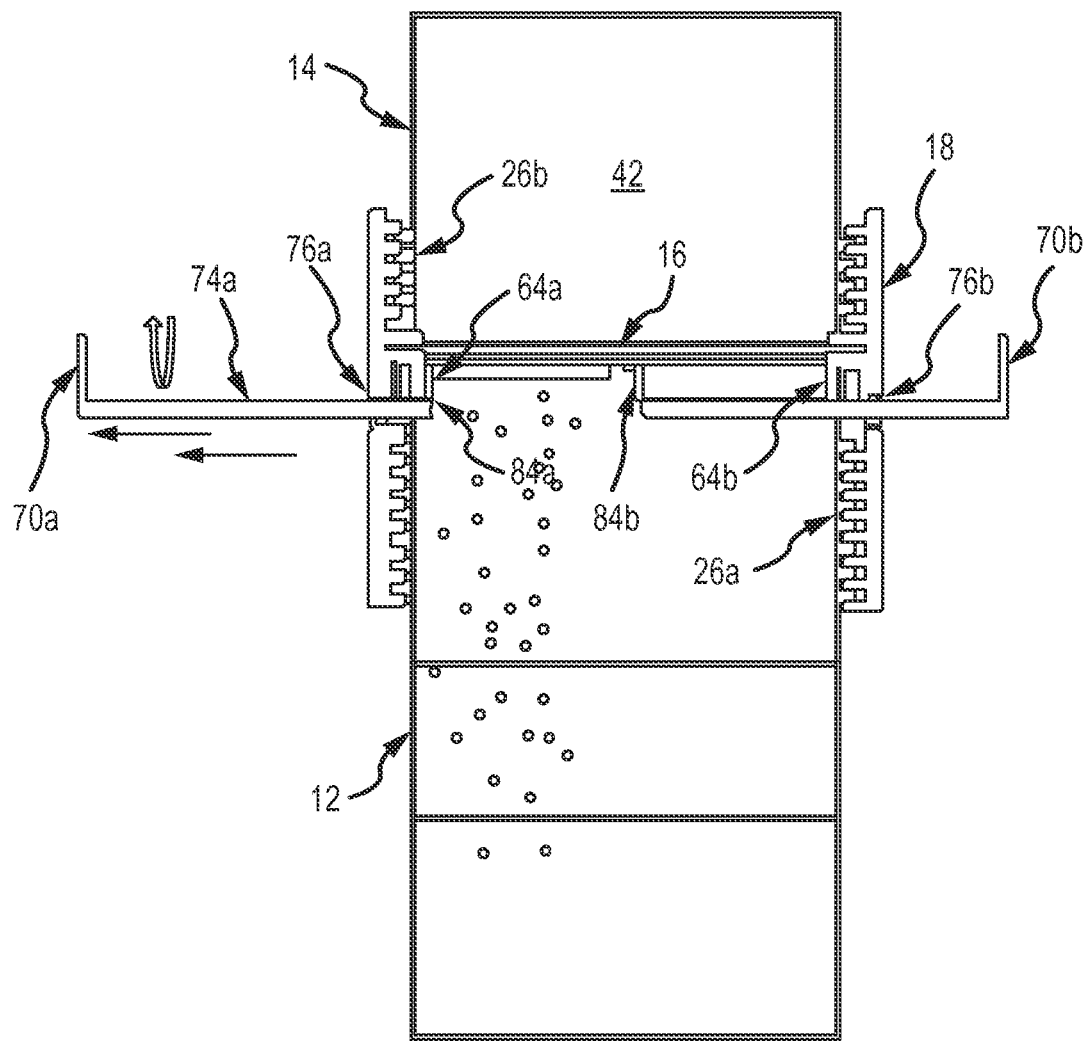
FIG. 11 is a schematic representation of a side view of the apparatus shown in FIG. 10 illustrating the addition of ferrate to the oxidation/detection vial.

FIG. 10 is a schematic representation of a side view of another embodiment of the apparatus for adding reagents using separator 18. Shown is the addition of two reagents using separator 18 onto which vials 12 and 14, not shown in FIG. 10, are attached using threads 26a and 26b, respectively. Inert, flexible bags, 66, and, 68, containing ferrate and acid, respectively, are mounted on shanks 74a and 74b of levers 70a and 70b, respectively. Materials such as Teflon lined polyester, for example, may be used for bags 66 and 68. Levers, 70a and 70b, terminate in flanges, 84a, and, 84b, respectively, and are adapted to slideably move through seals 76a and 76b, respectively, which may include at least one Teflon-coated O-ring, and provide a gas seal for separator 18. As seen in FIG. 11, when ferrate is to be added to vial 12, lever 70a is pulled outwardly such that flange 84a crushes bag 66 against the inner wall of separator 18, forcing bag 66 to burst and spill its contents into vial 12. When acid is to be added to vial 12, lever 70b is pulled outwardly and bag 68 is crushed against the inner wall of separator 18 until it bursts and spills its contents into vial 12.

The foregoing has been presented for purposes of illustration and description and is not intended to be exhaustive or limiting. Many modifications and variations are possible in light of the above teaching.

| FIGURE LEGEND | |
|---|---|
| 10 | Measurement Apparatus |
| 12 | Oxidation/Detection Vial |
| 14 | Detection Vial |
| 16 | $CO_2$ Permeable Conduit |
| 18 | Separator |
| 20 | Open End of Vial 12 |
| 22 | Open End of Vial 14 |
| 24a, b | Supports/Seals |
| 26a, b | Female Threads |
| 28 | Inner Surface of Separator |
| 30 | Male Threads on Vial 12 |
| 32 | Male Threads on Vial 14 |
| 34 | IR Spectrophotometer |
| 36 | Acid Container |
| 38 | Foil Seal |
| 40 | Acid |
| 42 | pH-Sensitive Indicator |
| 44a-d | Compressible Arms |
| 46a-d | Inert Seals |
| 48 | Cap for Vial 12 |
| 50 | Cap for Vial 14 |
| 52 | Movable Rod |
| 54 | Portion of Rod Interior to Vial |
| 56a-d | Seals |
| 58a, b | Chambers |
| 60a, b | Detents in Rod |
| 62 | Cylinder |
| 64 | Block |
| 66 | Acid Containing Bag |
| 68 | Oxidant Containing Bag |
| 70 | Lever |
| 72 | Piston |
| 74 | Shank |
| 76 | Seal |

FIGURE LEGEND

| 78 | Inert Foil |
| 80 | Inert Foil |
| 82 | Air Space |
| 84a, b | Flanges |

The invention claimed is:

1. An apparatus for analyzing total carbon and chemical oxygen demand in a sample, comprising:
a first vial having an open end and a wall defining a first interior region, containing a first chosen quantity of an acid disposed in the first interior region into which the sample is introduced;
means for introducing an inorganic base reagent into the first interior region comprising a first compressible tube;
means for introducing an oxidant reagent into the first interior region comprising a second compressible tube;
means for introducing an acid reagent into the first interior region comprising a third compressible tube; wherein the first, second, and third compressible tubes are arms which extend from an outer surface of the wall of the first vial; and wherein a first, second, and third inert seal are provided between the first, second, and third compressible tubes, respectively, and the first vial, such that when at least one arm is compressed, the respective inert seal is opened and the respective reagent is delivered into the first vial;
a second vial having an open end and a wall defining a second interior region, containing a second chosen quantity of a pH-sensitive indicator disposed in the second interior region separate from the oxidant; and
a separator comprising:
a first sealing portion adapted for being sealed to the open end of the first vial and forming a fluid-tight seal therewith;
an opposing second sealing portion adapted for being sealed to the open end of the second vial and forming a fluid-tight seal therewith; and
a carbon dioxide permeable, liquid impermeable conduit disposed between the first sealing portion and the second sealing portion of the separator.

2. The apparatus of claim 1, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

3. The apparatus of claim 1, further comprising a photometer for measuring the absorbance of the pH-sensitive indicator in the second vial.

4. The apparatus of claim 1, further comprising a photometer for measuring the absorbance of the oxidant in said first vial.

5. An apparatus for analyzing total carbon and chemical oxygen demand in a sample, comprising:
a first vial having an open end and a wall defining a first interior region into which the sample is introduced;
tubular means for introducing an oxidant reagent into the first interior region;
tubular means for introducing an acid reagent into the first interior region; wherein the tubular means are arms which extend from an outer surface of the wall of the first vial; and wherein a first and second inert seal are provided between the tubular means, respectively, and the first vial such that when at least one arm is compressed, the respective inert seal is opened and the respective reagent is delivered into the first vial;
a second vial an having an open end and a wall defining a second interior region containing a first chosen quantity of a pH-sensitive indicator disposed in the second interior region; and
a separator comprising:
a first sealing portion adapted for being sealed to the open end of the first vial and forming a fluid-tight seal therewith;
an opposing second sealing portion adapted for being sealed to the open end of the second vial and forming a fluid-tight seal therewith;
and a carbon dioxide permeable, liquid impermeable conduit disposed between the first sealing portion and the second sealing portion of the separator.

6. The apparatus of claim 5, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

7. The apparatus of claim 5, further comprising a photometer for measuring the absorbance of the pH-sensitive indicator in the second vial.

8. The apparatus of claim 5, further comprising a photometer for measuring the absorbance of the oxidant in said first vial.

9. An apparatus for analyzing total organic carbon and chemical oxygen demand in a sample, comprising:
a first vial having an open end and a wall defining a first interior region into which the sample and an oxidant are introduced; a compressible tubular arm which extends from an outer surface of the wall of the first vial; and wherein an inert seal is provided between the arm and the first vial such that when the arm is compressed, the inert seal is opened and an acidic reagent is delivered into the first vial;
a second vial an having an open end and a wall defining a second interior region containing a first chosen quantity of a pH-sensitive indicator disposed in the second interior region; and
a separator comprising:
a first sealing portion adapted for being sealed to the open end of the first vial and forming a fluid-tight seal therewith;
an opposing second sealing portion adapted for being sealed to the open end of the second vial and forming a fluid-tight seal therewith;
a carbon dioxide permeable, liquid impermeable conduit disposed between the first sealing portion and the second sealing portion of the separator.

10. The apparatus of claim 9, wherein the wall of the first vial is threaded in the region of the open end of the first vial, the wall of the second vial is threaded in the region of open end of the second vial, the first sealing portion of the separator is adapted to screw onto the threaded wall of the first vial, and the second sealing portion is adapted to screw onto the threaded wall of the second vial.

11. The apparatus of claim 9, further comprising a photometer for measuring the absorbance of the pH-sensitive indicator in the second vial.

12. The apparatus of claim 9, further comprising a photometer for measuring the absorbance of the oxidant in said first vial.

* * * * *